(12) United States Patent
Wahl et al.

(10) Patent No.: US 12,256,993 B2
(45) Date of Patent: Mar. 25, 2025

(54) METHOD AND DEVICE FOR DETERMINING A VISUAL PERFORMANCE

(71) Applicant: Carl Zeiss Vision International GmbH, Aalen (DE)

(72) Inventors: Siegfried Wahl, Donzdorf (DE); Peter Essig, Tübingen (DE); Yannick Sauer, Tübingen (DE); Alexander Leube, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/450,001

(22) Filed: Aug. 15, 2023

(65) Prior Publication Data

US 2023/0404395 A1 Dec. 21, 2023

Related U.S. Application Data

(63) Continuation of application No. PCT/EP2022/056308, filed on Mar. 11, 2022.

(30) Foreign Application Priority Data

Mar. 12, 2021 (EP) .................................... 21162274

(51) Int. Cl.
*A61B 3/113* (2006.01)
*A61B 3/02* (2006.01)
(Continued)

(52) U.S. Cl.
CPC .................................. *A61B 3/113* (2013.01)

(58) Field of Classification Search
CPC ......... A61B 3/02; A61B 3/102; A61B 3/1025; A61B 3/113; A61B 3/1015; A61B 3/103;
(Continued)

(56) References Cited

U.S. PATENT DOCUMENTS 5,461,435 A * 10/1995 Rootzen ................. A61B 3/024
351/224
7,287,857 B2 * 10/2007 Glaser .................... A61B 3/032
351/239
(Continued)

FOREIGN PATENT DOCUMENTS

EP  3730037 A1  10/2020
GB  2375821 A  11/2002
(Continued)

OTHER PUBLICATIONS

Watson et al., "Quest: A Bayesian adaptive psychometric method," Perception & Psychophysics, vol. 33, No. 2, pp. 113 to 120, Mar. 1983.
(Continued)

*Primary Examiner* — Dawayne Pinkney
(74) *Attorney, Agent, or Firm* — Tautz & Schuhmacher LLC; Georg Hasselmann (57) ABSTRACT

A computer-implemented method, a computer program, and a device for determining a visual performance of an eye of a person are disclosed. The method includes displaying to at least one eye of a person a visual stimulus configured to elicit at least one type of eye movement in the at least one eye of the person with at least one screen; tracking the at least one type of eye movements in the at least one eye of the person with at least one eye tracker; determining the visual performance of the at least one eye of the person by using at least one first piece of information about the at least one visual stimulus and at least one second piece of information about an occurrence of the at least one type of eye movements in the at least one eye of the person with at least one processing unit.

13 Claims, 2 Drawing Sheets

(51) Int. Cl.
*A61B 3/10* (2006.01)
*A61B 3/12* (2006.01)

(58) Field of Classification Search
CPC ....... A61B 3/1225; A61B 3/024; A61B 3/032; A61B 3/005; A61B 5/1101; A61B 3/022
USPC ............... 351/209, 200, 205, 206, 210, 211, 351/221–223, 237, 239, 240, 243, 351/245–246
See application file for complete search history.

(56) References Cited

U.S. PATENT DOCUMENTS

| | | | | |
|---|---|---|---|---|
| 7,918,558 | B1* | 4/2011 | Legerton | A61B 3/113 351/246 |
| 8,337,019 | B2* | 12/2012 | Murray | A61B 3/113 351/208 |
| 10,531,795 | B1* | 1/2020 | Abou Shousha | A61B 3/113 |
| 2008/0309880 | A1* | 12/2008 | Fisher | A61B 3/032 351/239 |
| 2013/0176534 | A1 | 7/2013 | Frankfort et al. | |
| 2016/0270656 | A1* | 9/2016 | Samec | G02B 27/0093 |
| 2017/0210010 | A1* | 7/2017 | Chen | A61B 5/374 |
| 2019/0038125 | A1* | 2/2019 | Lesmes | A61B 3/022 |
| 2020/0121179 | A1* | 4/2020 | Prusky | A61B 3/0091 |
| 2020/0305707 | A1 | 10/2020 | Fink et al. | |
| 2022/0039645 | A1 | 2/2022 | Leube et al. | |
| 2023/0148927 | A1* | 5/2023 | Chou | B60K 35/00 340/576 |

FOREIGN PATENT DOCUMENTS

| | | |
|---|---|---|
| WO | 2018006013 A1 | 1/2018 |
| WO | 2020216790 A1 | 10/2020 |
| WO | 2020260614 A1 | 12/2020 |

OTHER PUBLICATIONS

Leek et al., "Adaptive procedures in psychophysical research," Perception & Psychophysics, vol. 63, No. 8, pp. 1279 to 1292, Nov. 2001.

Engbert et al., "Microsaccades uncover the orientation of covert attention," Vision Research, vol. 43, No. 9, pp. 1035 to 1045, Apr. 2003.

Nyström et al., "An adaptive algorithm for fixation, saccade, and glissade detection in eyetracking data," Behavior Research Methods, vol. 42, No. 1, pp. 188 to 204, Feb. 2010.

Waddington et al., "Human optokinetic nystagmus and spatial frequency," Journal of Vision, vol. 15, No. 13, pp. 1 to 16, Sep. 2015.

Dakin et al., "Similar contrast sensitivity functions measured using psychophysics and optokinetic nystagmus," Scientific Reports, vol. 6, pp. 1 to 14, Oct. 2016.

Zemblys et al., "gazeNet: End-to-end eye-movement event detection with deep neural networks," Behavior Research Methods, vol. 51, No. 2, pp. 840 to 864, Mar. 2017.

Watson et al., "Quest+: A general multi dimensional Bayesian adaptive psychometric method," Journal of Vision, vol. 17, No. 3, pp. 1 to 27, Apr. 2017.

Bellet et al., "Human-level saccade detection performance using deep neural networks," Journal of Neurophysiology, vol. 121, No. 2, pp. 646 to 661, Feb. 2019.

European Search Report issued in EP 21 162 274.1, to which this application claims priority, mailed Sep. 13, 2021.

International Search Report and Written Opinion issued in PCT/EP2022/056308, to which this application claims priority, mailed May 25, 2022.

International Preliminary Report on Patentability issued in PCT/EP2022/056308, to which this application claims priority, mailed Jun. 5, 2023.

\* cited by examiner

METHOD AND DEVICE FOR DETERMINING A VISUAL PERFORMANCE

CROSS REFERENCE TO RELATED APPLICATIONS

This application is a continuation application of international patent application PCT/EP2022/056308, filed on Mar. 11, 2022 and designating the U.S., which claims priority to European patent application EP 21 162 274.1, filed on Mar. 12, 2021, both of which are hereby incorporated by reference in their entireties.

TECHNICAL FIELD

The present disclosure relates to a computer-implemented method, a computer program and a device for determining a visual performance of at least one eye of a person. Determining the visual performance, specifically at least one of a contrast sensitivity, a visual acuity, a color vision or a visual field, of the at least one eye of the person can, in particular, be used as examination method for at least one of an early detection of at least one visual impairment or an observation of a treatment success of the at least one visual impairment. However, further applications may also be feasible.

BACKGROUND

Known tests of the visual performance, specifically of the contrast sensitivity and/or the visual acuity, of one or both eyes of a person are, typically, used as an examination method for an early detection of at least one visual impairment and/or an observation of a treatment success of the at least one visual impairment. In practice, such tests may, typically, be executable with low cooperation of a person. Known tests, such as 'Hiding Heidi' or a LEA low-contrast symbol test, wherein gaze behavior is evaluated by an examiner to determine the contrast sensitivity, have been developed for persons with low cooperation. However, the LEA low-contrast symbol test still requires verbal report, and both of these tests can only be executed by a trained examiner and a minimum cooperation of the examined person.

R. Engbert and R. Kliegl, *Microsaccades uncover the orientation of covert attention*, Vision Research 43 (2003) 1035-1045, describes a saccade filter. Fixational eye movements are subdivided into tremor, drift, and microsaccades, wherein all three types of miniature eye movements generate small random displacements of the retinal image when viewing a stationary scene. The modulation of microsaccades have been investigated by shifts of covert attention in a classical spatial cueing paradigm. Firstly, they replicated a suppression of microsaccades with a minimum rate about 150 ms after cue onset; secondly, they observed microsaccadic enhancement with a maximum rate about 350 ms after presentation of the cue; and thirdly, they found a modulation of the orientation towards the cue direction.

M. Nyström and K. Holmqvist, *An adaptive algorithm for fixation, saccade, and glissade detection in eyetracking data*, Behavior Research Methods 2010, 42 (1), 188-204, described that event detection is used to classify recorded gaze points into periods of fixation, saccade, smooth pursuit, blink, and noise. They suggest a new velocity-based algorithm which identifies so-called glissades, a wobbling movement at the end of many saccades, as a separate class of eye movements. They propose designing an adaptive velocity threshold that makes the event detection less sensitive to variations in noise level and the algorithm settings-free for the user.

J. Waddington and C. M. Harris, *Human optokinetic nystagmus and spatial frequency*, Journal of Vision (2015) 15(13):7, 1-16, investigated the effect of stimulus spatial frequency (SP) on the stochastic processes of OKN. Increasing the spatial frequency of supra-threshold stimuli resulted in a significant increase in velocity of compensatory slow phases with a corresponding reduction in retinal slip. However, retinal slip rarely reached values close to zero, indicating that the OKN system does not or cannot always minimize retinal slip. They deduce that OKN gain must be less than unity if extraretinal gain is lower than unity, and that a difference between retinal and extraretinal gain determines Markov properties of SP velocity. As retinal gain is reduced with stimuli of lower spatial frequency, the difference between retinal and extraretinal gain increases and the Markov properties can be observed.

S. C. Dakin and P. R. K. Turnbull, *Similar contrast sensitivity functions measured using psychophysics and optokinetic nystagmus*, Scientific Reports, 2016, 6:34514, DOI: 10.1038/srep34514, describe a system for measuring the contrast sensitivity function (CSF) using an automated analysis of the OKN, in particular, a spatial-frequency (SF) band-pass noise. Quantifying the strength of the OKN in stimulus direction allows estimating the contrast sensitivity across a range of spatial frequencies. Herein, the CSFs was compared with normal vision measured using both OKN and perceptual report. These approaches yielded near-identical CSFs which capture subtle intra-observer variations in visual acuity and contrast sensitivity. Trial-by-trial analysis reveals high correlation between OKN and perceptual report, being a signature of a common neural mechanism for determining stimulus direction. They conclude that a wide range of stimulus conditions exist for which OKN can provide a valid alternative of measuring of the CSF.

A. B. Watson and D. G. Pelli, QUEST: *A Bayesian adaptive psychometric method*, Perception & Psychophysics, 1983, 33 (2), 113-120, and A. B. Watson, QUEST+: *A general multidimensional Bayesian adaptive psychometric method*, Journal of Vision (2017) 17(3):10, 1-27, describe a Bayesian adaptive psychometric testing procedure that allows an arbitrary number of stimulus dimensions, psychometric function parameters, and trial outcomes. Herein, QUEST+ is a generalization and extension of the original QUEST procedure which places each trial at a current most probable Bayesian estimate of threshold is described. These procedures take advantage of the common finding that the human psychometric function is invariant in form when expressed as a function of log intensity. QUEST+ incorporates many subsequent developments in the area of parametric adaptive testing, i.e. with a single procedure, it is possible to implement a wide variety of experimental designs, including conventional threshold measurement; measurement of psychometric function parameters, such as slope and lapse; estimation of the contrast sensitivity function; measurement of increment threshold functions; measurement of noise-masking functions; Thurstone scale estimation using pair comparisons; and categorical ratings on linear and circular stimulus dimensions.

M. R. Leek, *Adaptive procedures in psychophysical research*, Perception & Psychophysics, 2001, 63 (8), 1279-1292, describes the general development of adaptive procedures in psychophysical research, and reviews three commonly used methods. Typically, a threshold value is measured using these methods, and, in some cases, other characteristics of the psychometric function underlying perceptual performance, such as slope, may be developed.

M. E. Bellet, J. Bellet, H. Nienborg, Z. M. Hafed, and P. Berens, *Human-level saccade detection performance using deep neural networks*, J. Neurophysiol. 121: 646-661, 2019, present a convolutional neural network that can automatically identify saccades with human-level accuracy and with minimal training examples, offering an open-source implementation of the algorithm as well as a web service.

R. Zemblys, D. C. Niehorster, and Kenneth Holmqvist, *gazeNet: End-to-end eye-movement event detection with deep neural networks*, Behavior Research Methods, published online under doi.org/10.3758/s13428-018-1133-5, present *gazeNet*, which is a framework for creating event detectors that do not require hand-crafted signal features or signal thresholding. It employs an end-to-end deep learning approach which takes raw eye-tracking data as input and classifies it into fixations, saccades and post-saccadic oscillations. This method augments handcoded data, thus, strongly enlarging the data set used for training, minimizing the time spent on manual coding. Using this extended hand-coded data, a neural network has been trained that produces eye-movement event classification from raw eye-movement data without requiring any predefined feature extraction or post-processing steps.

U.S. Pat. No. 7,918,558 B1 discloses a method of measuring retinal or visual pathway function which comprises stimulating optokinetic nystagmus by presenting a visual stimulus to a patient; modifying a first parameter of the visual stimulus; modifying a second parameter of the visual stimulus; and using the modified visual stimulus to determine a threshold stimulus for optokinetic nystagmus; wherein the first and second parameters are selected from a group of parameters comprising a pattern for the visual stimulus, a width of the visual stimulus, a distance between the visual stimulus and the patient, a spatial frequency of the visual stimulus, a rate of change or temporal frequency of the test face of the visual stimulus, and a contrast between elements of the visual stimulus.

US 2013/0176534 A1 discloses a method for adaptively determining a model of visual performance of a test subject comprising the step of exposing a test subject to a plurality of trials. Each trial comprises the steps of identifying the stimulus pattern to test, generating a stimulus pattern on a display, determining whether the stimulus pattern generated an OKR, updating the model to incorporate the OKR results, and determining whether the updated model is acceptable. The trials can be iteratively repeated until the model for visual performance is acceptable.

WO 2018/006013 A1 discloses a system which can measure eye gaze position and detect, in near real-time, smooth eye movements that are driven by a moving stimulus. Smooth movements that match the velocity of a moving stimulus provide evidence that the subject can see the moving stimulus. The system can provide real-time feedback to the person, e.g. in the form of music, contingent on the ability of the person to perform smooth velocity-matched eye movements. The system can measure visual impairment and train visual ability both for rehabilitation and development purposes.

WO 2020/216790 A1 and EP 3 730 037 A1 disclose a method and a device for determining a refraction error of an eye of a user, wherein the method comprises: a) displaying a sign on a screen, wherein a parameter of the sign displayed on the screen is changed; b) tracking of an eye movement metrics of the eye of the user depending on a change of the sign displayed on the screen; c) determining a point in time at which a recognition threshold arises from the eye movement metrics of the eye of the user for the sign displayed on the screen; and d) determining a value for the refraction error of the eye of the user from the parameter at the point in time. In a particular embodiment, eye movement metrics which are based on OKN, in particular a correlation between phase or velocity of the stimulus on the screen with the compensatory slow phases of the OKN, can be used for determining whether the user recognizes the sign displayed on the screen as a stimulus or not.

WO 2020/260614 A1 discloses a method and a device for determining a contrast sensitivity threshold of eyes of a user and a related computer program product comprising executable instructions for performing the method. Herein, the method comprises the following steps:

a) providing a dataset of track data, wherein the track data comprise data of eye movements, wherein the eye movements are stimulated by a visual stimulus which is configured to elicit an optokinetic nystagmus in the at least one eye of the person, wherein the track data are related to a particular contrast and a particular spatial frequency of the stimulus; b) estimating at least one velocity component of the eye movement from the track data for the particular contrast and the particular spatial frequency of the stimulus; c) comparing the velocity component of the eye movement for the track data with a velocity threshold; d) further comparing a fraction of the track data which exceed the velocity threshold with a fractional threshold for the dataset, whereby the dataset which exceeds the fractional threshold is classified as eliciting the optokinetic nystagmus at the particular contrast of the stimulus; and e) determining the contrast sensitivity threshold of the eyes of the user. The method and the device allow determining the contrast sensitivity threshold of the eyes of the user in an automatic manner neither requiring an experienced examiner nor active attention of the user.

US 2020/305707 A1 discloses an apparatus, a software and methods for assessing ocular, ophthalmic, neurological, physiological, psychological and/or behavioral conditions. The conditions are assessed using eye-tracking technology that eliminates the need for a subject to fixate and maintain focus during testing or to produce a secondary (non-optical) physical movement or audible response, i.e., feedback. The subject is only required to look at a series of individual visual stimuli, which is generally an involuntary reaction. The reduced need for cognitive and/or physical involvement of a subject allows the present modalities to achieve greater accuracy, due to reduced human error, and to be used with a wide variety of subjects, including small children, patients with physical disabilities or injuries, patients with diminished mental capacity, elderly patients, animals, etc.

GB 2 375 821 A discloses a visual acuity testing system including a computer with a high-resolution display linked to a video camera. Vertical gratings of varying width are presented either side of a central target image or video, coincident with an iso-luminant image opposite the grating. A digital video camera adjacent to the display is employed to track eye position using software algorithms that relate eye movement to the position of the vertical grating. Software analysis adjusts for head movement, blinks and corneal reflexes. The system eliminates the need to lift acuity cards manually, and provides an automated and objective method of vision assessment in pre-verbal children and those unable to communicate in standard visual acuity tests.

SUMMARY

In particular with respect to the disclosure of GB 2 375 821 A, it is, therefore, an objective of the present disclosure to provide a computer-implemented method, a computer program and a device for determining a visual performance of at least one eye of a person, which at least partially overcome the above-mentioned problems of the state of the art.

It is a particular objective of the present disclosure to provide an automatic visual performance test which, compared to known visual performance tests, requires less time for performing the test, is particularly eye-friendly by reducing stress onto the at least one eye of the person, and can easily be performed by using a mobile communication device.

This problem is solved by a computer-implemented method, a computer program and a device for determining a visual performance of at least one eye of a person having the features of the independent claims. Exemplary embodiments, which might be implemented in an isolated fashion or in any arbitrary combination, are listed in the dependent claims and throughout the specification.

In a first aspect, the present disclosure relates to a computer-implemented method for determining a visual performance of at least one eye of a person. As used herein, the term "at least one eye" refers to a single eye of the person or to both eyes of the person. The method according to the present disclosure comprises the following steps a) to c):
  a) displaying to at least one eye of a person at least one visual stimulus configured to elicit at least one type of eye movements in the at least one eye of the person;
  b) tracking the at least one type of eye movements in the at least one eye of the person;
  c) determining the visual performance of the at least one eye of the person by using at least one first piece of information about the at least one visual stimulus and at least one second piece of information about an occurrence of the at least one type of eye movements in the at least one eye of the person,
wherein at least a part of the at least one visual stimulus is displayed in a time-varying manner independent of whether the at least one type of eye movements is elicited in the at least one eye of the person or not.

Herein, the indicated steps a) to c) may, typically, be performed in the given order, commencing with step a), continuing with step b), and finishing with step c). However, any or all of the indicated steps may be performed concurrently at least in part and/or be repeated several times. Further steps, whether described herein or not, can, in addition, also be performed in relationship with the present method.

As already indicated, the method according to the present disclosure is a computer-implemented method. As generally used, the term "computer-implemented method" refers to a method which involves a programmable apparatus, in particular a processing unit, specifically a computer, such as a stationary computer, a computer network, or a readable medium carrying a computer program, whereby at least one feature of the method is performed using the at least one computer program. Alternatively, the at least one computer program may be accessible by an apparatus configured to perform the method via at least one of:
  a network, such as an in-house network or the internet;
  a virtual reality device, such as a virtual reality headset;
  an augmented reality device, such as an augmented reality (AR) overlay; or
  a mobile communication device.

As generally used, the term "mobile communication device" refers to a smartphone, a tablet, or a laptop, which can be carried by the person and, can thus, move together with the person. However, further kinds of mobile communication devices may also be conceivable. Herein, the at least one mobile communication device may comprise at least one operating system that may be configured to facilitate a use of software, multimedia functionalities, and communication facilities, especially an access to internet or to at least one wireless communication protocol, such as Wi-Fi or Bluetooth.

As indicated above, the present method related to determining the visual performance of at least one eye of a person. As generally used, the term "determining" relates to a process of generating at least one representative result, in particular a plurality of representative results, with respect to the visual performance of the at least one eye of a person by applying the method as disclosed herein.

As further used herein, the term "visual performance" refers to a property of at least one eye of a person which can be determined by investigating the at least one eye of a person by an adapted measurement procedure. In particular, the visual performance can be selected from at least one property of the at least one eye of the person, in particular:
  a contrast sensitivity;
  a visual acuity;
  a color vision; or
  a visual field
of the at least one eye of the person. As generally used, the term "contrast sensitivity" refers to a property of at least one eye of a person to discern between different luminance levels in at least one visual stimulus. As further generally used, the term "visual acuity" refers to a spatial resolution of the at least one eye of the person with respect to a structure within at least one visual stimulus. As further generally used, the term "color vision" refers to a property of the at least one eye of the person to discern between different colors comprised by at least one visual stimulus. As further generally used, the term "visual field" refers to a spatial array that can be viewed by the at least one eye of the person, in particular, when intending to focus the view on a particular item, such as a fixation cross. Furthermore, each property of the at least one eye of the person can, alternatively or in addition, be determined in at least one of a static fashion or a dynamic fashion. As used in this regard, the term "static" refers to at least one single value of the respective property at a particular point in time, while the term "dynamic" refers to a plurality of values representing a temporal course of the respective property.

In addition, at least one further property of the at least one eye of the person may be determined by using the visual performance of the at least one eye of the person as determined in accordance with the method as disclosed herein, specifically at least one refractive error of the at least one eye of the person from the corresponding contrast sensitivity. As generally used, the terms "refraction" or "refractive" refer to a bending of incident light entering the interior of the eye of the person via the pupil, wherein the term "refractive error" refers to an observation that the incident light may, in particular owing to a form of the eye, not be focusing appropriately on the retina of the eye, resulting in a defocus of the eye. In particular, the contrast sensitivity as a function of spatial frequency follows a characteristic curve, wherein a shape of the curve, especially a slope of the curve, changes with the defocus of the person. From measurements of the contrast sensitivity for at least two different spatial frequencies, the shape of the contrast sensitivity function can be associated with the defocus, i.e. with the refractive error of the eye.

According to step a), at least one visual stimulus which is configured to elicit at least one type of eye movements in at least one eye of a person is displayed to the at least one eye of the person. As used herein, the term "visual stimulus" refers to a graphical presentation of at least one pattern or image which is known or reasonably be expected by the person skilled in the art to elicit the at least one desired type of eye movements in the at least one eye of the person. Typically, the at least one visual stimulus may be comprised by at least one of:

a natural image comprising the at least one visual stimulus; or at least one of an artificial pattern, or a virtual environment comprising the at least one visual stimulus in form of at least one computer-generated visual stimulus.

As used herein, the term "natural image" refers to a picture having been captured from a scene occurring in nature. By way of example, the natural image may be a picture of a landscape or of an interior scene, such as of a room or a part thereof. In contrast hereto, the term "artificial pattern" relates to a computer-generated pattern while the term "virtual environment" refers to a scene that is generated by using a computer program, typically, in a fashion that it may resemble and/or reconstruct a naturally occurring scene. In a simple example, the artificial pattern may be or comprise a plurality of stripes, such as a pattern of alternating black and white stripes. In a more elaborated example, the at least one visual stimulus may be comprised by an interior scene showing a part of a room, in which a curtain covering a portion of a window may be rapidly moving due to a blast of wind. In still a more elaborated example, the at least one visual stimulus may be comprised by a virtual environment showing a picture of a woodland in which the trees may maintain their position and in which the leaves may move in arbitrary fashion around their correspondingly fixed positions, while an animal which may be rapidly moving through the woodland. In a still further example, the virtual environment may be or comprise a gaming environment, such as, typically, used in designing a computer game. However, still further examples a conceivable.

In particular, the computer-generated stimulus may be selected from at least one of a computer-generated static stimulus or a computer-generated dynamic stimulus. As used in this regard, the term "static" refers to a kind of visual stimulus which is presented to the person in an unamended fashion, typically, as long as the person views at this kind of visual stimulus. In contrast hereto, the term "dynamic" refers to a kind of visual stimulus which is presented to the person in a time-varying manner, in particular in a fashion that a least a part of this kind of visual stimulus varies its appearance during it is viewed by the person.

As generally used, the term "eye movements" refers to a motion of one or both eyes of a person. Apart from spontaneous eye movements, the movement of the eyes of the person can be triggered by at least one visual stimulus, in particular by the at least one stimulus as described above. For recording the motions of the at least one eye, at least one eye tracker may, typically, be used for generating monocular track data or, typically, binocular track data. According to the present disclosure, the at least one type of eye movements that can be elicited by using the at least one visual stimulus can be selected from at least one of:

fixational eye movements;

pursuit eye movements; or an optokinetic nystagmus, wherein the tracking of the at least one optokinetic nystagmus the at least one eye of the person may comprise a saccade detection and a slow phase velocity thresholding, wherein the optokinetic nystagmus may, particularly, be utilized.

As generally used, the term "fixational eye movements" refer to a first kind of eye movements intended to focus the view of the eyes of the person on a particular item, such as a fixation cross. As further generally used, the term "pursuit eye movements" refer to a further kind of eye movements intended to follow a moving item by the eyes of the person. As further generally used, the terms "optokinetic nystagmus" or "OKN" refer to a reflexive movement of the eyes of a person which is generated as a response to a homogeneous optic flow. In the OKN, involuntary slow pursuit movements also denoted as "compensatory slow phases" alternate with saccadic quick phases or "saccades."

For eliciting the OKN, the at least one visual stimulus may, in particular, exert a motion in at least one direction. Typically, the OKN may be triggered by using an artificial pattern as described above that is specifically designed for this purpose. By way of example, a virtual representation of a so-denoted "OKN drum" can be used for eliciting the OKN in the eyes of the person, whereby the OKN drum may, typically, be presented as virtual reality to the person, especially by using at least one of a virtual reality headset, an augmented reality (AR) overlay, or a mobile communication device. As generally used, the term "OKN drum" refers to a rotatable cylindrical object being covered with a pattern of alternating black and white stripes which is turned in front of the eyes of the person, specifically by rotating the cylinder clockwise or anticlockwise.

As a result of eliciting the OKN, a desired saccadic eye movement can be generated in which the successive execution of slow pursuit movements and saccadic quick phases can be clearly visible. Herein, the desired saccadic eye movement can be a horizontal saccadic eye movement. In a similar manner, other kinds of OKN movements, such as a vertical saccadic eye movement or a combination thereof with the horizontal saccadic eye movement, can also be generated. As generally used, the term "horizontal" refers to a direction which is provided by a connecting line which connects both eyes, in particular both pupils of the eyes, of a person. Similarly, the term "vertical" refers to a direction which is perpendicular to a horizontal direction and parallel to a direction of gravity. In an exemplary embodiment of the present disclosure, at least one different visual stimulus can be used for eliciting the saccadic motion of the eye in a horizontal direction and in a vertical direction.

According to the present disclosure, at least a part of the at least one visual stimulus is displayed in a time-varying manner. As used herein, the term "time-varying manner" refers to presenting the at least one visual stimulus in a fashion that the at least one visual stimulus or the at least one part thereof varies an appearance to the eyes of the person over time. As further used herein, the term "part" refers to at least one portion of the at least one stimulus which is varied over time, while other portions of the at least one stimulus, in particular the remaining portions of the at least one visual stimulus, may be maintained in a fixed position. With respect to the above-mentioned simple example in which the artificial pattern may be or comprise a plurality of stripes, such as a pattern of alternating black and white stripes, the plurality of stripes may be moving in a fashion to be able to elicit the desired type of eye movements. In the more elaborated example as further described above, the interior scene showing a stationary part of a room may, thus, not be capable of eliciting the desired type of eye movements, while the rapidly moving curtain may be capable of eliciting the desired type of eye movements. In the still more elaborated example as further described above, in which the at least one visual stimulus may be a virtual environment showing a picture of a woodland, wherein the trees may maintain their position and the leaves may move in arbitrary fashion around their correspondingly fixed positions and may, thus, not be capable of eliciting the desired type of eye movements, the animal rapidly moving through the woodland may be capable of eliciting the desired type of eye movements. Further examples a feasible.

According to the present disclosure, the time-varying manner may, typically, comprise continuously modifying the at least one part of the at least one visual stimulus, wherein the continuously modifying of the at least one part of the at least one visual stimulus may, in particular, comprise continuously varying at least one value of at least one parameter for at the at least one part of the at least one visual stimulus. As generally used, the term "parameter" refers to a property of the at least one part of the at least one visual stimulus depending on the selected visual stimulus which can, specifically, be expressed by using a particular numerical or alphanumerical value. Typically, the at least one parameter may be selected from at least one of:
  a contrast, in particular for determining the contrast sensitivity;
  a spatial frequency, in particular for determining the visual acuity;
  a color, including black and white, in particular for determining the color vision; or
  a spatial location, in particular for determining the visual field; and
  a temporal frequency, in particular for determining a dynamic contrast sensitivity or a dynamic visual acuity.

Herein, the temporal frequency may, in particular, be used for determining a temporal frequency threshold in a spatiotemporal contrast sensitivity curve.

As generally used, the term "contrast" refers to a luminance level in the at least one visual stimulus. As further generally used, the term "spatial frequency" refers to a reciprocal value of a spatial distance reflecting a spatial period of repetition in the at least one visual stimulus. As further generally used, the term "color" refers to a wavelength of a pattern as used in the at least one visual stimulus. As further generally used, the term "spatial location" refers to a location within the at least one visual stimulus.

In particular accordance with the present disclosure, the at least a part of the at least one visual stimulus is displayed in a time-varying manner independent of whether the at least one type of eye movements is elicited in the at least one eye of the person or not. In particular, the modifying of the at least one part of the at least one visual stimulus in the time-varying manner is independent from the tracking of the at least one type of eye movements in the at least one eye of the person according to step b) as described below in more detail. As used herein, the phrase "independent of whether the at least one type of eye movements is elicited in the at least one eye of the person or not" indicates that the displaying of the at least one visual stimulus is performed in a manner that at least one particular visual stimulus is selected to be presented to the eyes of the person without considering any current or previous results as obtained from the tracking of the at least one type of eye movements in the at least one eye of the person.

In particular, continuously varying of the at least one value of the at least one parameter for the at least one part of the at least one visual stimulus may comprise increasing or decreasing the at least one value for the at least one parameter for the at least one part of the at least one visual stimulus. On one hand, the increasing of the at least one value for the at least one parameter may, typically, be performed between a lower value and an upper value, typically in a monotonous manner. On the other hand, the decreasing of the at least one value for the at least one parameter may, typically, performed between an upper value and a lower value, typically in a monotonous manner. As generally used, the term "monotonous" refers to a type of variation in which a sign of a first derivative of the variation does not change during the course of variation.

Rather, the at least one particular visual stimulus is selected by applying considerations for ascertaining the lower value, the upper value, and the value for the first derivative of the variation. In particular, the upper value for the at least one parameter may be selected in a fashion that the at least one type of eye movements is elicited in the at least one eye of the person, wherein the lower value for the at least one parameter may be selected in a fashion that the same type of eye movements is not elicited in the at least one eye of the person. The value for the first derivative of the variation may, typically, be chosen to allow a fast measurement of the at least one desired property, wherein the speed of variation may, however, be limited to obtain an initial threshold value at which the at least one type of eye movements is elicited in the at least one eye of the person for a first time or a terminal threshold value at which the at least one type of eye movements is elicited in the at least one eye of the person for a last time with a desired resolution.

According to step b), the at least one type of eye movements is tracked in the at least one eye of the person. As generally used, the term "tracking" refers to recording motions of the at least one eye, typically, by using at least one eye tracker. As a result, a dataset of track data is provided, wherein the dataset comprises a multitude of track data. Herein, the term "track data" refers to a plurality of data items which comprise either measured values or values which are derived from measured values, wherein the measured values are related to movements of the eyes of the person. Herein, monocular track data can be generated for a single eye of the person or, typically, binocular track data for both eyes of the person. Specifically, the measured values can be video images of the at least one eye, such as video images having a reflex on the cornea, wherein a signal can, typically, be a relative position of the reflex to an ocular pupil, being extracted from the video images, whereas the data item can be a value, such a position or a particular pixel on a screen, which has been derived from the video images, such as by using a calibrated function. Herein, the data item can be at least one single value, such as a single value, a doublet of values, or a triplet of values, wherein the value may be a numerical value or an alphanumerical value. However, the data item may comprise further values, typically values for a particular contrast and a particular spatial frequency of the stimulus applied for eliciting the eye movement of which the corresponding track data are recorded.

As indicated above, the tracking of the at least one type of eye movements in the at least one eye of the person may, typically, comprise identifying an initial threshold value at which the at least one type of eye movements is elicited in the at least one eye of the person for a first time; and a terminal threshold value at which the at least one type of eye movements is elicited in the at least one eye of the person for a last time.

Accordingly, at least one of the initial threshold value, the terminal threshold value, or a combination thereof, typically at least one mean value as determined from of the initial threshold value and the terminal threshold value, especially at least one of an arithmetic mean value, a geometric mean value, or a harmonic mean value, may, typically, be used as a threshold value for determining the at least one second piece of information about the occurrence of the at least one type of eye movements in the at least one eye of the person.

According to step c), the visual performance of the at least one eye of the person is determined by using at least one first piece of information about the at least one visual stimulus and at least one second piece of information about an occurrence of the at least one type of eye movements in the at least one eye of the person. In particular, the visual performance of the at least one eye of the person may be determined by using the at least one first piece of information about the at least one visual stimulus at a point in time as identified by the at least one second piece of information about the occurrence of the at least one type of eye movements in the at least one eye of the person. As generally used, the term "piece of information" refers to a data set which comprises at least one value for a desired property.

By way of example, the second piece of information may comprise a threshold value which has been determined according to step b) in a fashion as described above or below in more detail. The threshold value as comprised by the second piece of information may indicate a point in time related to a first occurrence or to a last occurrence of a particular type of eye movements in the at least one eye of the person. The at least one value for the at least one parameter related to the visual stimulus configured to elicit the particular type of eye movements in the at least one eye of the person as displayed to at least one eye of a person according to step a) is, subsequently, used as the first piece of information in order to determine the visual performance of the at least one eye of the person according to step c).

Herein, the visual performance of the at least one eye of the person may, in an exemplary embodiment, be determined concurrently with the tracking of the at least one type of eye movements in the at least one eye of the person according to step b). In a further embodiment, the visual performance of the at least one eye of the person may, alternatively or in addition, be determined at any point in time after the tracking the at least one type of eye movements in the at least one eye of the person according to step b). As an advantage of the further embodiment, the track data can be recorded according to step b) by using at least one eye tracker on a less sophisticated virtual reality headset, augmented reality (AR) overlay, or mobile communication device, wherein the determining of the visual performance of the at least one eye of the person according to step c) can be performed on a sophisticated processing unit, typically comprised by at least one of a remote server or a cloud server, at any time after the track data have been recorded and transmitted to the sophisticated processing unit. However, further manners of determining the visual performance of the at least one eye of the person according to step c) may also be conceivable.

In a particular embodiment, steps a) to c) may be repeated by using at least one different visual stimulus configured to elicit the at least one type of eye movements or at least one different type of eye movements in the at least one eye of the person. Herein, the at least one different visual stimulus differs from the at least one visual stimulus by at least one of at least one different value for the at least one parameter for the at least one part of the at least one visual stimulus; or at least one different parameter for the at least one part of the at least one visual stimulus.

In a particular embodiment, different visual stimuli may be used for eliciting a motion of the eye in a horizontal direction and in a vertical direction, respectively. Herein, the visual performance of the at least one eye of the person can be determined separately for a horizontal eye movement and a vertical eye movement, wherein the horizontal eye movement may follow the motion of the visual stimulus in the horizontal direction, and wherein the vertical eye movement may follow the motion of the visual stimulus in the vertical direction. In this embodiment, the different visual stimuli for eliciting the motion of the eye in the horizontal direction and in the vertical direction can be applied in a serial manner. However, other manners of elicitation may also be feasible, such as applying the visual stimulus within a plane perpendicular to a direction of view of the person.

In a further aspect, the present disclosure relates to a computer program comprising instructions which, when the program is executed by a computer, cause the computer to carry out the method according to any one of the preceding method embodiments. Specifically, the computer program may be stored on a computer-readable data carrier. Thus, specifically, any one of the method steps as indicated above may be performed by using a computer or a computer network, typically by using a computer program.

In a further aspect, the present disclosure relates to a computer program product having program code means, in order to perform the methods according to the present disclosure when the program is executed on a computer or computer network. Specifically, the program code means may be stored on a computer-readable data carrier.

In a further aspect, the present disclosure relates to a data carrier having a data structure stored thereon, which, after loading into a computer or computer network, such as into a working memory or main memory of the computer or computer network, may execute any one of the methods according to one or more of the embodiments disclosed herein.

In a further aspect, the present disclosure relates to a computer program product with program code means stored on a machine-readable carrier, in order to perform the methods according to one or more of the embodiments disclosed herein, when the program is executed on a computer or computer network. As used herein, the term "computer program product" refers to the program as a tradable product. The product may generally exist in an arbitrary format, such as in a paper format, or on a computer-readable data carrier. Specifically, the computer program product may be distributed over a data network, such as the internet.

In a further aspect, the present disclosure relates to a modulated data signal which comprises instructions readable by a computer system or computer network, for performing any one of the methods according to one or more of the embodiments as disclosed herein.

In a further aspect, the present disclosure relates to a device for determining a visual performance of at least one eye of a person. Herein, the device comprises at least one screen for displaying at least one visual stimulus designated for eliciting at least one type of eye movements in at least one eye of the person;

at least one screen eye tracker for identifying whether the at least one type of eye movements is elicited in the at least one eye of the person or not; and at least one processing unit, wherein the processing unit is designated for determining the visual performance of the at least one eye of the person by using at least one first piece of information about the at least one visual stimulus and at least one second piece of information about an occurrence of the at least one type of eye movements in the at least one eye of the person, wherein the at least one screen is designated for displaying at least a part of the at least one visual stimulus in a time-varying manner independent of whether the at least one type of eye movements is elicited in the at least one eye of the person or not.

In an exemplary embodiment of the present disclosure, the at least one screen, the at least one eye tracker, and the at least one processing unit may be integrated in a virtual reality headset. Alternatively, the at least one processing unit can partially be comprised by a mobile communication device, which may be in communication with the virtual reality headset. As generally used, the term "virtual reality headset" refers to a head-mounted device which is designated for providing virtual reality for the person who wears the virtual reality headset. In general, the virtual reality headset comprises a stereoscopic head-mounted display which may be capable of providing separate images for each eye; stereo sound; a head motion tracking sensor, such as a gyroscope, an accelerometer, or a structured light system; and an eye tracking sensor.

In an exemplary embodiment, the at least one screen, the at least one eye tracker and the at least one processing unit may be comprised by a mobile communication device. For the term "mobile communication device" reference may be made to the definition above. In addition, the mobile communication device may, further, comprises least one sensor, in particular, selected from a gyroscope, an accelerometer, or a proximity sensor.

In a further exemplary embodiment, the at least one screen and the at least one eye tracker may be integrated in smart glasses whereas the at least one processing unit can be comprised by a mobile communication device in communication with the smart glasses. As generally used, the term "smart glasses" refers to glasses which are wearable by a person and which are designed for superimposing information onto a field of view of the person. Further, the smart glasses may be designated for changing optical properties when worn by the person. For these purposes, embedded wireless glasses with a transparent heads-up display or an augmented reality (AR) overlay may be used which, on one hand, allow a usual visual reception by the person and, on the other hand, are designed for projecting digital images provided by integrated applications.

Alternatively or in addition, further embodiments with respect to the device according to the present disclosure are conceivable.

With respect to the prior art, the method and the device according to the present disclosure exhibit the following advantages.

According to the present disclosure a whole interval of different values for the at least one parameter of the at least one visual stimulus can be applied in a time-saving fashion. In particular contrast hereto, US 2013/0176534 A1 as referenced above, discloses a method for measuring visual performance based on OKN by changing the stimulus parameter between trials using adaptive psychometric procedures. In principle, adaptive stimulus parameters are time efficient but this method always requires a detection of OKN during or after the trial, each time based on a decision whether the OKN actually occurs or not. In a particular embodiment, the eye movements are analyzed in real time and the stimulus parameter can be adapted according to the current OKN situation without breaks between trials. However, applying a live detection of eye movements in addition to using adaptive procedures can be computationally challenging, making resulting in particular problems for applications using a mobile communication device.

In particular owing to the use of the whole interval of different values, the visual performance of the at least one eye of the person can be determined in accordance with the present disclosure during a single procedure without having a necessity to, consecutively, adjust the at least one value for the at least one parameter depending on already obtained results in preceding procedures with at least one different value for the at least one parameter, which may be particularly boring to the person of whom the visual performance of the at least one eye may be determined. Thus, the method according to the present disclosure may, especially, be suited for children of any age, for teenagers, elderly persons, or handicapped persons.

The method and the device according to the present disclosure may, further, be advantageous since it allows splitting the determining of the visual performance according to step c) from the tracking of the track data according to step b). In particular, the track data can be recorded during the step b) by using a particular kind of eye tracker that readily available to the person, such as a front camera of a smartphone, but by performing the step c) on a sophisticated processing unit, such as comprised by a remote server and/or a cloud server, at any time after the track data have been recorded and transmitted to the sophisticated processing unit. As a result, the method and the device according to the present disclosure can, thus, be performed on low-budget smartphone having a less sophisticated processing unit but comprising an ordinary communication unit for data exchange with the sophisticated processing unit.

Further, existing methods of repeated trials with parameters approaching the performance threshold may be, particularly, demanding for the patient, since stimulus parameters close to a threshold require persistent concentration and may be especially stressful for the eyes of the person. The method and the device according to the present disclosure, however, reduces possible stress to the eyes of the patient by presenting continuously varied levels of stimulus parameters, not only parameters which are close to the threshold.

In addition, further advantages may also be conceivable.

As used herein, the terms "have," "comprise" or "include" or any arbitrary grammatical variations thereof are used in a non-exclusive way. Thus, these terms may refer to both a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

As further used herein, the terms "typically," "more typically," "particularly," "more particularly," or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in this way with other features of the disclosure.

Summarizing, the exemplary embodiments according to the following Clauses are particularly typical within the scope of the present disclosure:

Clause 1: A computer-implemented method for determining a visual performance of at least one eye of a person, the method comprising the following steps:
  a) displaying to at least one eye of a person at least one visual stimulus configured to elicit at least one type of eye movements in the at least one eye of the person;
  b) tracking the at least one type of eye movements in the at least one eye of the person;
  c) determining the visual performance of the at least one eye of the person by using at least one first piece of information about the at least one visual stimulus and at least one second piece of information about an occurrence of the at least one type of eye movements in the at least one eye of the person,
wherein at least a part of the at least one visual stimulus is displayed in a time-varying manner independent of whether the at least one type of eye movements is elicited in the at least one eye of the person or not.

Clause 2: The method according to the preceding Clause, wherein the visual performance is selected from at least one of:
  a contrast sensitivity;
  a visual acuity;
  a color vision; or
  a visual field.

Clause 3: The method according to any one of the preceding Clause, wherein the time-varying manner comprises continuously modifying the at least one part of the at least one visual stimulus.

Clause 4: The method according to the preceding Clause, wherein the continuously modifying of the at least one part of the at least one visual stimulus is independent from the tracking of the at least one type of eye movements in the at least one eye of the person.

Clause 5: The method according to any one of the two preceding Clauses, wherein the continuously modifying of the at least one part of the at least one visual stimulus comprises continuously varying at least one value of at least one parameter for the at least one part of the at least one visual stimulus.

Clause 6: The method according to the preceding Clause, wherein the at least one parameter is selected from at least one of:
  a contrast, in particular for determining the contrast sensitivity;
  a color, in in particular for determining the color vision
  a spatial frequency, in particular for determining the visual acuity;
  a spatial location, in particular for determining a visual field; or
  a temporal frequency, in particular for determining a dynamic contrast sensitivity or a dynamic visual acuity.

Clause 7: The method according to the preceding Clause, wherein the temporal frequency is used for determining a temporal frequency threshold in a spatio-temporal contrast sensitivity curve.

Clause 8: The method according to any one of the three preceding Clauses, wherein the continuously varying of the at least one value of the at least one parameter for the at least one part of the at least one visual stimulus comprises increasing or decreasing the at least one value for the at least one parameter for the at least one part of the at least one visual stimulus.

Clause 9: The method according to the preceding Clause, wherein the increasing of the at least one value is performed between a lower value and an upper value, typically in a monotonous manner.

Clause 10: The method according to any one of the two preceding Clauses, wherein the decreasing of the at least one value is performed between an upper value and a lower value, typically in a monotonous manner.

Clause 11: The method according to any one of the three preceding Clauses, wherein the upper value is selected to elicit the at least one type of eye movements in the at least one eye of the person.

Clause 12: The method according to any one of the four preceding Clauses, wherein the lower value is selected not to elicit the at least one type of eye movements in the at least one eye of the person.

Clause 13: The method according to any one of the preceding Clauses, wherein determining the at least one second piece of information about the occurrence of the at least one type of eye movements in the at least one eye of the person comprises identifying an initial threshold value at which the at least one type of eye movements is elicited in the at least one eye of the person for a first time.

Clause 14: The method according to any one of the preceding Clauses, wherein determining the at least one second piece of information about the occurrence of the at least one type of eye movements in the at least one eye of the person comprises identifying a terminal threshold value at which the at least one type of eye movements is elicited in the at least one eye of the person for a last time.

Clause 15: The method according to any one of the two preceding Clauses, wherein at least one of:
  the initial threshold value;
  the terminal threshold value; or
  a combination thereof,
is used as a threshold value for determining the at least one second piece of information.

Clause 16: The method according to the preceding Clause, wherein the combination of the initial threshold value and the terminal threshold value comprises at least one mean value determined from the initial threshold value and the terminal threshold value.

Clause 17: The method according to the preceding Clause, wherein the at least one mean value is selected from at least one of
  an arithmetic mean value;
  a geometric mean value; or
  a harmonic mean value.

Clause 18: The method according to any one of the preceding Clauses, wherein the visual performance of the at least one eye of the person is determined by using the at least one first piece of information at a point in time as identified by the at least one second piece of information.

Clause 19: The method according to any one of the preceding Clauses, wherein the visual performance of the at least one eye of the person is determined at at least one of:
concurrently with the tracking of the at least one type of eye movements in the at least one eye of the person; or
at any point in time after the tracking of the at least one type of eye movements in the at least one eye of the person.

Clause 20: The method according to any one of the preceding Clauses, wherein steps a) to c) are repeated by using at least one different visual stimulus configured to elicit the at least one type of eye movements or at least one different type of eye movements in the at least one eye of the person.

Clause 21: The method according to the preceding Clause, wherein at least one different visual stimulus differs from the at least one visual stimulus by at least one of:
at least one different value for the at least one parameter for the at least one part of the at least one visual stimulus; or
at least one different parameter for the at least one part of the at least one visual stimulus.

Clause 22: The method according to any one of the preceding Clauses, wherein the at least one visual stimulus is comprised by at least one of:
a natural image; or
at least one of an artificial pattern or a virtual environment which comprises at least one computer-generated stimulus comprises, wherein the computer-generated stimulus is selected from at least one of a computer-generated static stimulus or a computer-generated dynamic stimulus.

Clause 23: The method according to any one of the preceding Clauses, wherein the at least one type of eye movements is selected from at least one of:
fixational eye movements;
pursuit eye movements; or
an optokinetic nystagmus.

Clause 24: The method according to the preceding Clause, wherein the tracking of the at least one optokinetic nystagmus the at least one eye of the person comprises a saccade detection and a slow phase velocity thresholding.

Clause 25: The method according to any one of the preceding Clauses, further comprising a step of
d) measuring a distance between a screen which displays the at least one visual stimulus and the at least one eye of the person; or Clause 26: The method according to any one of the preceding Clauses, further comprising a step of
e) measuring a luminance level of the at least one visual stimulus, wherein the visual performance of the at least one eye of the person is determined by using a measured value for the luminance level of the visual stimulus.

Clause 27: The method according to any one of the preceding Clauses, further comprising a step of
f) determining at least one refractive error of the at least one eye of the person by using the visual performance of the at least one eye of the person.

Clause 28: A computer program comprising instructions which, when the program is executed by a computer, cause the computer to carry out the method for determining a visual performance of at least one eye of a person according to any one of the preceding method steps.

Clause 29: A device for determining a visual performance of at least one eye of a person, the device comprising:
at least one screen, wherein the at least one screen is designated for displaying to at least one eye of a person at least one visual stimulus configured to elicit at least one type of eye movements in the at least one eye of the person;
at least one eye tracker, wherein the at least one eye tracker is designated for tracking the at least one type of eye movements in the at least one eye of the person; and
at least one processing unit, wherein the at least one processing unit is designated for determining the visual performance of the at least one eye of the person by using at least one first piece of information about the at least one visual stimulus and at least one second piece of information about an occurrence of the at least one type of eye movements in the at least one eye of the person,
wherein the at least one screen is designated for displaying at least a part of the at least one visual stimulus in a time-varying manner independent of whether the at least one type of eye movements is elicited in the at least one eye of the person or not.

Clause 30: The device according to the preceding Clause, wherein the at least one screen is designated for displaying the at least one part of the at least one visual stimulus by continuously modifying the at least one part of the at least one visual stimulus.

Clause 31: The device according to any one of the preceding device Clauses, wherein the processing unit is further designated for using at least one of
the initial threshold value;
the terminal threshold value; or
a combination thereof
as a threshold value for determining the at least one second piece of information about the occurrence of the at least one type of eye movements in the at least one eye of the person.

Clause 32: The device according to the preceding Clause, wherein the processing unit is further designated for determining at least one mean value from the initial threshold value and the terminal threshold value as the combination of the initial threshold value and the terminal threshold value.

Clause 33: The device according to the preceding Clause, wherein the at least one mean value is selected from at least one of
an arithmetic mean value;
a geometric mean value; or
a harmonic mean value.

Clause 34: The device according to the preceding Clause, wherein the processing unit is further designated for using the at least one first piece of information at a point in time as identified by the at least one second piece of information.

Clause 35: The device according to any one of the preceding device Clauses, wherein the screen and the eye tracker are integrated in at least one of
a virtual reality headset;
an augmented reality system;
smart glasses; or
a mobile communication device,
wherein the processing unit is comprised by at least one of the virtual really headset, the augmented reality system, or the mobile communication device.

Clause 36: The device according to any one of the preceding device Clauses, wherein the at least one screen is designated for displaying at least one of a natural image comprising the at least one visual stimulus; or at least one of an artificial pattern or a virtual environment, wherein the at least one of the artificial pattern or the virtual environment comprises at least one computer-generated stimulus, wherein the at least one computer-generated stimulus is selected from at least one of a computer-generated static stimulus or a computer-generated dynamic stimulus.

Clause 37: The device according to any one of the preceding device Clauses, further comprising at least one distance measuring unit configured to measure a distance between the screen displaying the at least one visual stimulus and the at least one eye of the person.

Clause 38: The device according to any one of the preceding device Clauses, further comprising at least one illumination sensor configured to measure a luminance level of the at least one visual stimulus, wherein the processing unit is further designated for determining the visual performance of the at least one eye of the person by using a measured value for the luminance level of the visual stimulus.

Clause 39: The device according to any one of the preceding device Clauses, further comprising at least one communication unit.

Clause 40: The device according to the preceding Clause, wherein the at least one communication unit is configured to at least one of forward data related to the tracking of the at least one type of eye movements in the at least one eye of the person to at least one external storage unit and to receive the data related to the tracking of the at least one type of eye movements from the at least one external storage unit for further processing by the processing unit;

forward data related to the tracking of the at least one type of eye movements in the at least one eye of the person and further data related to the visual stimulus configured to elicit the at least one type of eye movements in the at least one eye of the person to at least one external processing unit and to receive still further data related to the visual performance of the at least one eye of the person from the at least one external processing unit.

Clause 41: The device according to the preceding Clause, wherein the at least one external storage unit is comprised by at least one of a local server, a remote server, or a cloud server.

Clause 42: The device according to any one of the two preceding Clauses, wherein the at least one external processing unit is comprised by at least one of a local server, a remote server, or a cloud server.

BRIEF DESCRIPTION OF THE DRAWINGS

Further optional features and exemplary embodiments of the present disclosure are disclosed in more detail in the subsequent description of exemplary embodiments. Therein, the respective optional features may be realized in an isolated fashion as well as in any arbitrary feasible combination, as the skilled person will realize. It is emphasized here that the scope of the disclosure is not restricted by the exemplary embodiments.

The disclosure will now be described with reference to the drawings wherein.

DESCRIPTION OF EXEMPLARY EMBODIMENTS

Figure 1:
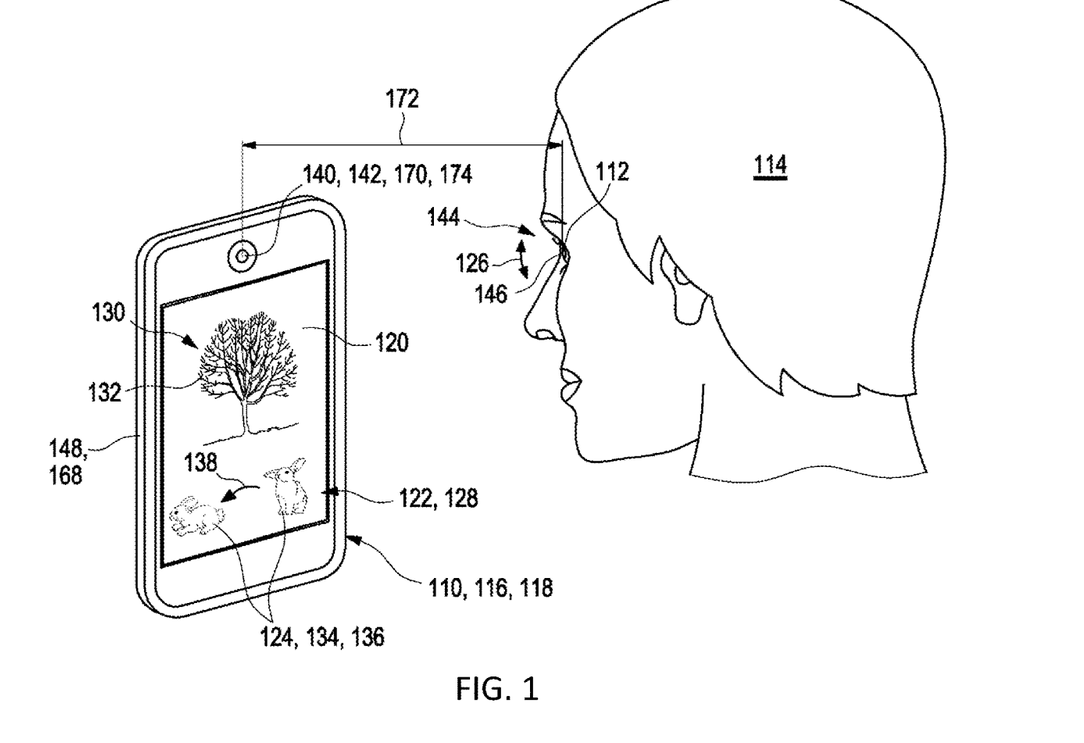
FIG. 1 illustrates an exemplary embodiment of a device for determining a visual performance of at least one eye of a person according to the present disclosure.

FIG. 1 shows an exemplary embodiment of a device 110 for determining a visual performance of one or both eyes 112 of a person 114. In the illustration according to FIG. 1 and in the following description, the device 110 is implemented—without limiting the generality of the disclosure—as a mobile communication device 116 in form of a smartphone 118. However, implementing the device 110 in form of a stationary computer or a different type of mobile communication device 116, in particular a tablet or a laptop, may also feasible.

As already defined above, the visual performance refers to a property of the one or both eyes 112 of the person 114 which can be determined by investigating of the one or both eyes 112 of the person 114 by an adapted measurement procedure. For the purposes of the present disclosure, the visual performance can be selected from one or more properties of the one or both eyes 112 of the person 114, in particular from:

a contrast sensitivity;
a visual acuity;
a color vision; or
a visual field of the one or both eyes 112 of the person 114. For the respective terms, reference can be made to the definitions as provided above. Furthermore, each of the mentioned properties can, alternatively or in addition, be determined a static fashion and/or a dynamic fashion.

As further illustrated in FIG. 1, the smartphone 118 comprises a screen 120 which is designated for displaying at least one scene 122 to the one or both eyes 112 of the person 114, wherein the at least one scene 122 comprises at least one visual stimulus 124 which is configured to elicit at least one type of eye movements 126 in the one or both eyes 112 of the person 114. As schematically depict in FIG. 1, the scene 122 comprises a natural image or a virtual environment displaying a picture of a woodland scene 128 in which a tree 130 maintains its position and in which leaves 132 move in arbitrary fashion around their correspondingly fixed positions. As a result, neither the tree 130 nor the leaves 132 may be capable of eliciting the desired type of the eye movements 126. In contrast hereto, an animal 134, such as a rabbit 136, is rapidly moving as indicated by an arrow 138 through the woodland scene 128 and is, therefore, capable of eliciting the desired type of the eye movements 126. As indicated above, various types of further examples a conceivable.

As already described above, the visual stimulus 124 is designed for eliciting the desired type of the eye movements 126 in the one or both eyes 112 of the person 114. Herein, the visual stimulus 124 may be selected from one or more of fixational eye movements, pursuit eye movements, or an optokinetic nystagmus, wherein the pursuit eye movements or the optokinetic nystagmus may, particularly be utilized in the exemplary embodiment as shown in FIG. 1 in order to achieve that the one or both eyes 112 of the person 114 may follow the rapidly moving animal 134, specifically the rabbit 136 as indicated by the arrow 138.

Further, the smartphone 118 comprises an eye tracker 140, wherein the eye tracker 140 is designated for tracking the type of the eye movements 126 in the one or both eyes 112 of the person 114. As schematically illustrated in FIG. 1, the eye tracker 140 can be implemented by using a front camera 142 of the smartphone 118. For this purpose, the front camera 142 of the smartphone 118 can record a plurality of images of an eye area 144 of the person 114 covering pupils 146 of the one or both eyes 112 of the person 114, wherein the tracking of the type of the eye movements 126 in the one or both eyes 112 of the person 114 can be determined from the plurality of the images of the eye area 144 of the person 114. However, using a separate tracking device (not depicted here) which can, typically, be mounted at a side of the one or both eyes 112 of the person 114 in order to record the type of the eye movements 126 of the one or both eyes 112 of the person 114 individually. Still, further examples are conceivable.

Further, the smartphone 118 comprises a processing unit 148 which is designated for determining the visual performance of the one or both eyes 112 of the person 114 by using a first piece of information about the visual stimulus 124 and at least one second piece of information about an occurrence of the at least one type of the eye movements 126 in the one or both eyes 112 of the person 114. For further details concerning the processing unit 148, reference can be made to the description above.

In particular accordance with the present disclosure, the visual stimulus 124 is displayed to the one or both eyes 112 of the person 114 in a time-varying manner independent of whether the at least one type of the eye movements 126 is actually elicited in the one or both eyes 112 of the person 114 or not. In particular, the modifying of the visual stimulus 124 over time is independent from the tracking of the type of the eye movements 126 in the one or both eyes 112 of the person 114. In other words, the visual stimulus 124 is presented to the one or both eyes 112 of the person 114 without considering any current or previous results as obtained from the tracking of the type of the eye movements 126 in the one or both eyes 112 of the person 114.

Rather, the time-varying manner which is used for displaying the visual stimulus 124 to the one or both eyes 112 of the person 114 may, typically, comprise a continuously modifying of the visual stimulus 124. Herein, the visual stimulus 124 may be modified in a complete fashion, such as by letting the rabbit 136 run over the screen 120 as schematically depicted in FIG. 1. Alternatively or in addition, only a part of the visual stimulus 124 may be modified, such as by moving ears of the rabbit 136. In particular, the continuously modifying of the visual stimulus 124 may, typically, comprise continuously varying a value of one or more parameters for the visual stimulus 124 or the part thereof. Specifically, the parameter may be selected from one or more of:

- a contrast, in particular for determining the contrast sensitivity;
- a spatial frequency, in particular for determining the visual acuity;
- a color, including black and white, in particular for determining the color vision; or
- a spatial location, in particular for determining the visual field; or
- a temporal frequency, in particular for determining a dynamic contrast sensitivity or a dynamic visual acuity.

Herein, the temporal frequency may, in particular, be used for determining a temporal frequency threshold in a spatio-temporal contrast sensitivity curve.

Figure 2A:
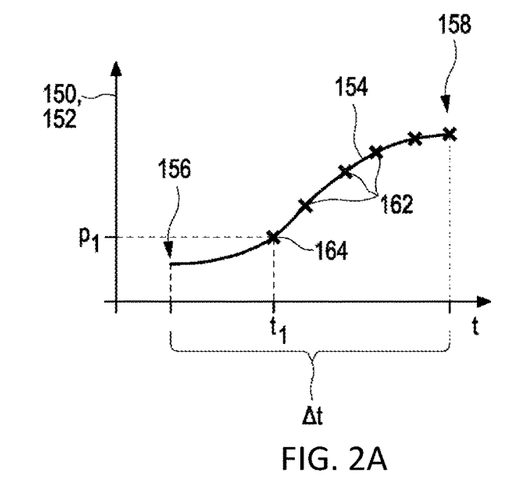
FIGS. 2A and 2B illustrate courses showing an increase (FIG. 2A) or a decrease (FIG. 2B), respectively, of values of a parameter of a visual stimulus over a period of time as for determining the visual performance of the at least one eye of the person according to the present disclosure.

In particular, the continuously varying of the value of the one or more parameters for the visual stimulus 124 or the part thereof may comprise increasing or decreasing the value for the one or more parameters for the visual stimulus 124 or the part thereof. FIG. 2A schematically illustrates for a particular parameter 150, such as a contrast 152 of the visual stimulus 124, a first course 154 showing an increase of the value of the parameter 150, such as the contrast 152, of the visual stimulus 124, over a period of time $\Delta t$ between a lower value 156 and an upper value 158 in a monotonous manner. In the exemplary scene 122 as depicted in FIG. 1, the rabbit 136 may, especially, show an increasing contrast 152 during it may run over the screen 120.

Figure 2B:
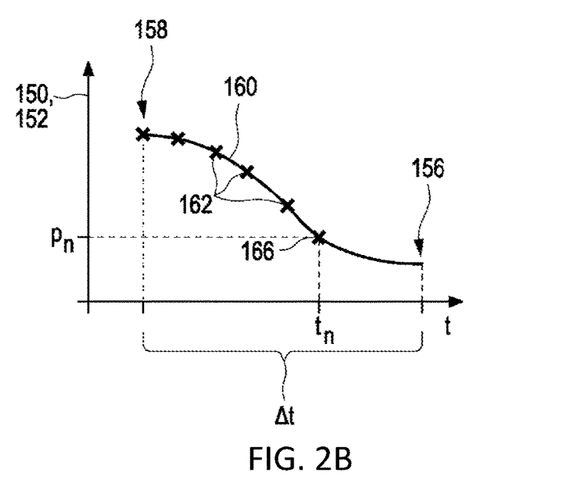

In a similar fashion, FIG. 2B schematically illustrates for the particular parameter 150, such as the contrast 152, of the visual stimulus 124, a second course 160 showing a decrease of the value of the parameter 150, such as the contrast 152, of the visual stimulus 124, over the period of time $\Delta t$ between the upper value 158 and the lower value 156 also in a monotonous manner. In the exemplary scene 122 as depicted in FIG. 1, the rabbit 136 may, especially, show a decreasing contrast 152 during it may run over the screen 120.

Alternatively or in addition to varying the contrast 152 for determining the visual sensitivity, any one of the spatial frequency, in particular for determining the visual acuity; the color, including black and white, in particular for determining the color vision; the spatial location, in particular for determining the visual field; and/or the temporal frequency, in particular for determining a dynamic contrast sensitivity or a dynamic visual acuity, may be varied.

In dependent of the selected parameter, the upper value 158 for the parameter 150 of the visual stimulus 124 may, typically, be selected in a fashion that the type of the eye movements 126 may be elicited in the one or both eyes 112 of the person 114 at this particular value of the parameter 150, wherein the lower value 156 for the parameter 150 of the visual stimulus 124, may, typically, be selected in a fashion that the same type of the eye movements 126 is not elicited in the one or both eyes 112 of the person 114 at this particular value of the parameter 150.

By applying the visual stimulus 124 or the part thereof to the one or both eyes 112 of the person 114 by using the continuously varying values for the parameter 152 according to the first course 154 as depicted in FIG. 2A, the eye tracker 140, such as the front camera 142 of the smartphone 118, can observe an eliciting of the desired type of the eye movements 126 in the images of the eye area 144 of the person 114 covering the one or both eyes 112 of the person 114 at various occasions which are denoted in FIGS. 2A and 2B by the reference sign 162, starting with a first eliciting 164 at a first time $t_1$, whereby an initial threshold value $p_1$ may be defined, and continuing until the upper value 158 for the parameter 150 of the visual stimulus 124 may eventually be reached.

In a similar fashion, the visual stimulus 124 or the part thereof can be applied to the one or both eyes 112 of the person 114 by using the continuously varying values for the parameter 152 according to the second course 160 as depicted in FIG. 2B. As a result, the eye tracker 140, such as the front camera 142 of the smartphone 118, can observe the eliciting of the desired type of the eye movements 126 in the images of the eye area 144 of the person 114 covering the one or both eyes 112 of the person 114 at various occasions denoted by the reference sign 162, starting from the upper value 158 until a last eliciting 166 at a last time $t_n$ for the parameter 150 of the visual stimulus 124 may eventually be reached, whereby a terminal threshold value $p_n$ may be defined.

Further, a value for the first derivative of the first course 154 and the second course 160, respectively, may, typically, be chosen to allow, on one hand, a fast measurement of the variation of the parameter 150 of the visual stimulus 124 and, on the other hand, to obtain the initial threshold value $p_1$ and/or the terminal threshold value $p_n$ may with a desired resolution.

Typically, the initial threshold value $p_1$ or the terminal threshold value $p_n$ may be used as a threshold value when determining a second piece of information about an occurrence of the type of the eye movements 126 in the one or both eyes 112 of the person 114. Alternatively, a combination of the initial threshold value $p_1$ and the terminal threshold value $p_n$ may, typically, be used, wherein the combination may, typically, comprise a mean value determined from the initial threshold value $p_1$ and the terminal threshold value $p_n$, especially an arithmetic mean value, a geometric mean value, and/or a harmonic mean value. However, a further kind of determining the second piece of information about an occurrence of the type of the eye movements 126 in the one or both eyes 112 of the person 114 may also be conceivable.

In order to determine the visual performance of the one or both eyes 112 of the person 114, a first piece of information about the visual stimulus 124 is used, wherein the first piece of information about the visual stimulus 124 is given at a point in time as identified by the second piece of information. As particularly illustrated in FIG. 2A, the initial threshold value $p_1$ corresponds to the first time $t_1$ of tracking the eliciting of the desired type of the eye movements 126 the one or both eyes 112 of the person 114, wherein the value for the first time $t_1$ can be used for accessing the value for the parameter that has been used at the first time $t_1$ for generating the visual stimulus 124 that elicited the desired type of the eye movements 126 in the one or both eyes 112 of the person 114 for the first time. In a similar fashion as illustrated in FIG. 2B, the terminal threshold value $p_n$ corresponds to the last time $t_n$ of tracking the eliciting of the desired type of the eye movements 126 the one or both eyes 112 of the person 114, wherein the value for the last time $t_n$ can be used for accessing the value for the parameter that has been used at the last time $t_n$ for generating the visual stimulus 124 that elicited the desired type of the eye movements 126 in the one or both eyes 112 of the person 114 for the last time.

As a consequence, the value for the parameter that has been used for generating the visual stimulus 124 that only just elicited the desired type of the eye movements 126 in the one or both eyes 112 of the person 114 can be determined in this manner by using the value for the parameter applied at the first time $t_1$ and/or for at the last time $t_n$. Alternatively, a combination of the values for the parameter applied at the first time $t_1$ and at the last time $t_n$ may, typically, be used, wherein the combination may, typically, comprise one or more mean values which can be determined from the initial threshold value $p_1$ and the terminal threshold value $p_n$, especially selected from an arithmetic mean value, a geometric mean value, or a harmonic mean value. However, a further kind of determining the first piece of information about the visual stimulus 124 may also be conceivable.

In a typical exemplary embodiment of the present disclosure, the visual performance of the one or both eyes 112 of the person 114 may be determined in a concurrent fashion with the tracking of the type of the eye movements 126 in the one or both eyes 112 of the person 114. For this purpose, the processing unit 148 may be designated for determining the visual performance of the one or both eyes 112 of the person 114 by using the first piece of information about the visual stimulus 124 and the second piece of information about the occurrence of the type of the eye movements 126 in the one or both eyes 112 of the person 114, in particular for using the first piece of information at the point in time identified by the second piece of information as described above in more detail.

Alternatively or in addition, the visual performance of the one or both eyes 112 of the person 114 may be determined at any point in time after the tracking of the type of the eye movements 126 in the one or both eyes 112 of the person 114. For this purpose, the processing unit 148 may, further, comprise a communication unit 168 which may, in particular, be configured to forward data related to the tracking of the type of the eye movements 126 in the one or both eyes 112 of the person 114 to one or more external storage units (not depicted here) and to receive the data related to the tracking of the type of the eye movements 126 from the one or more external storage units for further processing by the processing unit 148. Alternatively or in addition, the communication unit 168 may, in particular, be configured to forward the data related to the tracking of the type of the eye movements 126 in the one or both eyes 112 of the person 114 and further data related to the visual stimulus 124 configured to elicit the type of the eye movements 126 in the one or both eyes 112 of the person 114 to one or more external processing units and to receive still further data related to the visual performance of the one or both eyes 112 of the person 114 from the one or more external processing units. Herein, the one or more external storage units and/or the one or more external processing units may, typically, be comprised by at least one of a local server, a remote server, or a cloud server.

The exemplary smartphone 118 as schematically depicted in FIG. 1 may, further, comprise a distance measuring unit 170, which may be configured to measure a distance 172 between the screen 120 displaying the visual stimulus 124 and the one or both eyes 112 of the person 114. As depicted there, the front camera 142 of the smartphone 118 can be used as the distance measuring unit 170. As already described above, the front camera 142 may record a plurality of images of the eye area 144 of the person 114 covering the pupils 146 of the one or both eyes 112 of the person 114, which can, alternatively or in addition, be used for measuring the distance 172 between the screen 120 and the one or both eyes 112 of the person 114.

The exemplary smartphone 118 as schematically depicted in FIG. 1 may, further, comprise a luminance sensor 174, which may be configured to measure a luminance level of the visual stimulus 124. As further depicted there, the front camera 142 of the smartphone 118 can be used as the luminance sensor 174. Based on at least one further piece of data related to the luminance level of the visual stimulus 124, the processing unit 148 and/or the one or more external processing unit may, further, be designated for determining the visual performance of the one or both eyes 112 of the person 114 by using a measured value for the luminance level of the visual stimulus 124. In this fashion, the values related to the contrast sensitivity can be determined as an absolute contrast sensitivity value by, additionally, taking into account the luminance level of the stimulus 124 as measured by the luminance sensor 174.

In further embodiments (not depicted here), the screen 120 and the eye tracker 140 may be integrated a virtual reality headset, an augmented reality system, and/or smart glasses as described above in more detail, wherein the processing unit may be comprised by the virtual really headset, by the augmented reality system, and/or by the mobile communication device which may in communication with the virtual reality headset, the augmented reality system, and/or the smart glasses. However, further embodiments may also be feasible.

Figure 3:
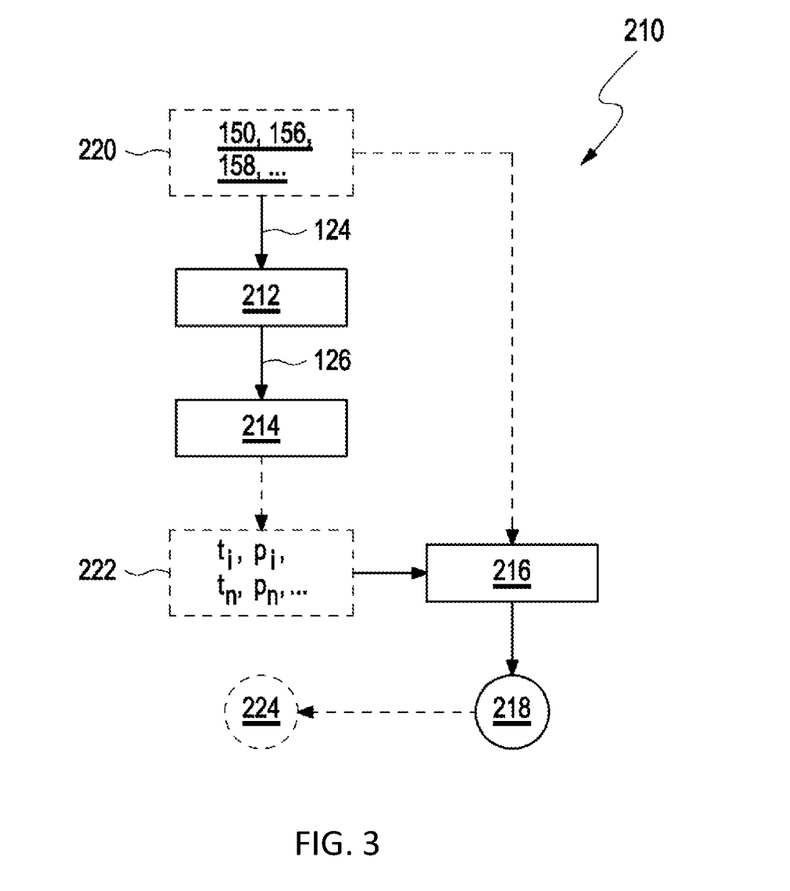
FIG. 3 illustrates an exemplary embodiment of a method for determining a visual performance of at least one eye of a person according to the present disclosure.

FIG. 3 schematically illustrates an exemplary embodiment of a method 210 for determining the visual performance of the one or both eyes 112 of the person 114 according to the present disclosure. As indicated above, the visual performance refers to a property of one or both eyes 112 of the person 114 which can be determined by investigating one or both eyes 112 of the person 114 by using an adapted measurement procedure. In particular, the visual performance can be selected from one or more properties of the one or both eyes 112 of the person 114, in particular from a contrast sensitivity, a visual acuity, a color vision, or a visual field of the one or both eyes 112 of the person 114. For the respective terms, reference can be made to the definitions as provided above. Furthermore, each of the mentioned properties can, alternatively or in addition, be determined a static fashion and/or a dynamic fashion.

In a displaying step 212 according to step a), the visual stimulus 124 is displayed to the one or both eyes 112 of the person 114, particularly by using the screen 120 of the smartphone 118, wherein the visual stimulus 124 is configured to elicit the type of eye the movements 126 in the one or both eyes 112 of the person 114.

In a tracking step 214 according to step b), the type of the eye movements 126 in the one or both eyes 112 of the person 114 are tracked, particularly by using the eye tracker 140, specifically the front camera 142 of the smartphone 118.

In a determining step 216 according to step c), a visual performance 218 of the one or both eyes 112 of the person 114 is determined by using a first piece of information 220 about the visual stimulus 124 and a second piece of information 222 about an occurrence of the type of the eye movements 126 in the one or both eyes 112 of the person 114.

In particular accordance with the present disclosure, the visual stimulus 124 or a part of the visual stimulus 124 is displayed, particularly by using the screen 120 of the smartphone 118, in a time-varying manner independent of whether the type of the eye movements 126 is elicited in the one or both eyes 112 of the person 114. In particular contrast to known methods for determining the visual performance of the one or both eyes 112 of the person 114, which, typically, use a selected finite number of values, such as two, three, four, five, six, eight, ten or twelve different values, for the parameter 150 of the visual stimulus 124, the values for the parameter 150 of the visual stimulus 124 as displayed during step a) is selected by applying considerations for ascertaining the lower value 156, the upper value 158, and the value for the first derivative of the variation between the lower value 156 and the upper value 158, or vice-versa.

As a result, a whole interval of different values for the parameter 150 of the visual stimulus 124 is applied in a time-saving fashion. In particular owing to the use of the whole interval of different values, the visual performance of the one or both eyes 112 of the person 114 can be determined in a single procedure without having a necessity to, consecutively, adjust the values for the parameter 150 depending on already obtained results in preceding procedures with one or more different values for the parameter 150, which may be particularly boring to the person 114 of whom the visual performance of the one or both eyes 112 is determined. The method 210 according to the present disclosure may, therefore, especially be suited for children of any age, for teenagers, elderly persons, or handicapped persons.

The method 210 and the device 110 according to the present disclosure may, further, be advantageous since it allows splitting the determining step 216 from the tracking step 214, specifically by recording the track data during the tracking step 214 by using a particular kind of eye tracker that may be readily available to the person 114, such as the front camera 142 of the smartphone 118, but by performing the determining step 216 on a sophisticated processing unit which may, typically, be comprised by a remote server and/or a cloud server, at any time after the track data have been recorded and transmitted to the sophisticated processing unit. The method 210 and the device 110 according to the present disclosure may, therefore, be particularly suited for persons having a low-budget smartphone.

In a particular embodiment, the visual performance 218 of the one or both eyes 112 of the person 114 as determined by using the method 210 as disclosed herein can, typically, be used for determining one or more further properties of the one or both eyes 112 of the person 114. Specifically, one or more refractive errors 224 of the one or both eyes 112 of the person 114 can be determined from the contrast sensitivity as determined by using the method 210. For further details in this respect, reference can be made to the description above.

In a further particular embodiment, any one or all of the displaying step 212, the tracking step 214, and the determining step 216 may be repeated once or more than once by using one or more different visual stimuli configured to elicit the same type of the eye movements 126 or one or more different types of eye movements in the one or both eyes 112 of the person 114. Herein, the one or more different visual stimuli may differ from the visual stimulus 124 by one or more different values for the one or more parameters for visual stimulus 124 or the part thereof. Alternatively or in addition, the one or more different visual stimuli may differ from the visual stimulus 124 by being capable of eliciting a different type of eye movements. However, further alternatives may also be conceivable.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term comprising (and its grammatical variations) as used herein is used in the inclusive sense of having or including and not in the exclusive sense of consisting only of. The terms a and the as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

List of Reference Signs 110 device for determining a visual performance of at least one eye of a person 112 eyes
114 person
116 mobile communication device
118 smartphone
120 screen
122 scene
124 stimulus
126 eye tracker
128 woodland scene
130 tree
132 leaves
134 animal
136 rabbit
138 arrow
140 eye tracker
142 front camera
144 eye area
146 pupil
148 processing unit
150 parameter
152 contrast
154 first course
156 lower value
158 upper value
160 second course
162 eliciting occasion
164 first eliciting
166 last eliciting
168 communication unit
170 distance measuring unit
172 distance
174 luminance sensor
210 method for determining a visual performance of at least one eye of a person
212 displaying step
214 tracking step
216 determining step
218 visual performance
220 first piece of information
222 second piece of information
224 refractive error

The invention claimed is:

1. A computer-implemented method for determining a visual performance of at least one eye of a person, the method comprising the following steps:
  a) displaying to the at least one eye of the person at least one visual stimulus configured to elicit at least one type of eye movements in the at least one eye of the person by using at least one screen;
  b) tracking the at least one type of eye movements in the at least one eye of the person by using at least one eye tracker;
  c) determining the visual performance of the at least one eye of the person by using at least one first piece of information about the at least one visual stimulus and at least one second piece of information about an occurrence of the at least one type of eye movements in the at least one eye of the person by using at least one processing unit,
    wherein at least a part of the at least one visual stimulus is displayed in a time-varying manner,
    wherein the at least one visual stimulus is presented in a manner that the at least one part of the at least one visual stimulus varies an appearance of the at least one visual stimulus to the at least one eye of the person over time, independent of whether the at least one type of eye movements is elicited in the at least one eye of the person or not,
    wherein the time-varying manner comprises continuously modifying the at least one part of the at least one visual stimulus by increasing or decreasing at least one value for the at least one parameter for the at least one part of the at least one visual stimulus between a lower value and an upper value in a monotonous manner, or between the upper value and the lower value in a monotonous manner,
    wherein the upper value is selected to elicit the at least one type of eye movements in the at least one eye of the person,
    wherein the lower value is selected not to elicit the at least one type of eye movements in the at least one eye of the person, and
    wherein continuously modifying the at least one part of the at least one visual stimulus is performed as a variation in which a sign of a first derivative of the variation does not change during the course of the variation.

2. The method according to claim 1, wherein the visual performance is selected from at least one of:
  a contrast sensitivity;
  a visual acuity;
  a color vision; or
  a visual field.

3. The method according to claim 1, wherein the time-varying manner comprises continuously modifying the at least one part of the at least one visual stimulus, and
  wherein the continuously modifying of the at least one part of the at least one visual stimulus is independent from the tracking of the at least one type of eye movements in the at least one eye of the person according to step b).

4. The method according to claim 3, wherein the continuously modifying of the at least one part of the at least one visual stimulus comprises continuously varying at least one value of at least one parameter for the at least one part of the at least one visual stimulus, and
  wherein the at least one parameter is selected from at least one of:
  a contrast;
  a color;
  a spatial frequency;
  a spatial location; or
  a temporal frequency.

5. The method according to claim 1, wherein determining the at least one second piece of information about the occurrence of the at least one type of eye movements in the at least one eye of the person comprises:
  identifying an initial threshold value at which the at least one type of eye movements is elicited in the at least one eye of the person for a first time; or
  identifying a terminal threshold value at which the at least one type of eye movements is elicited in the at least one eye of the person for a last time, and
  wherein at least one of
    the initial threshold value;
    the terminal threshold value; or
    at least one mean value determined from of the initial threshold value and the terminal threshold value
  is used as a threshold value for determining the at least one second piece of information.

6. The method according to claim 1, wherein the visual performance of the at least one eye of the person is determined by using the at least one first piece of information at a point in time as identified by the at least one second piece of information.

7. The method according to claim 1, wherein the visual performance of the at least one eye of the person is determined at at least one of:
concurrently with the tracking of the at least one type of eye movements in the at least one eye of the person; or
at any point in time after the tracking of the at least one type of eye movements in the at least one eye of the person.

8. The method according to claim 1, wherein the at least one visual stimulus is comprised by at least one of:
a natural image; or
at least one of an artificial pattern or a virtual environment which includes at least one computer-generated stimulus, and
wherein the computer-generated stimulus is selected from at least one of a computer-generated static stimulus or a computer-generated dynamic stimulus.

9. The method according to claim 1, wherein the at least one type of eye movements is selected from at least one of:
fixational eye movements;
pursuit eye movements; or
an optokinetic nystagmus, wherein the tracking of the at least one optokinetic nystagmus of the at least one eye of the person includes a saccade detection and a slow phase velocity thresholding.

10. The method according to claim 1, further comprising a step of at least one of:
d) measuring a distance between a screen which displays the at least one visual stimulus and the at least one eye of the person;
e) measuring a luminance level of the at least one visual stimulus, wherein the visual performance of the at least one eye of the person is determined by using a measured value for the luminance level of the visual stimulus; or
f) determining at least one refractive error of the at least one eye of the person by using the visual performance of the at least one eye of the person.

11. A computer program stored on a non-transitory storage medium and having instructions which, when the program is executed by a computer, cause the computer to carry out the method for determining a visual performance of at least one eye of the person, wherein the method comprises the following steps:
a) displaying to at least one eye of a person at least one visual stimulus configured to elicit at least one type of eye movements in the at least one eye of the person by using at least one screen;
b) tracking the at least one type of eye movements in the at least one eye of the person by using at least one eye tracker;
c) determining the visual performance of the at least one eye of the person by using at least one first piece of information about the at least one visual stimulus and at least one second piece of information about an occurrence of the at least one type of eye movements in the at least one eye of the person by using at least one processing unit,
wherein at least a part of the at least one visual stimulus is displayed in a time-varying manner,
wherein the at least one visual stimulus is presented in a manner that the at least one part of at the least one visual stimulus varies an appearance of the at least one visual stimulus to the at least one eye of the person over time, independent of whether the at least one type of eye movements is elicited in the at least one eye of the person or not,
wherein the time-varying manner includes continuously modifying the at least one part of the at least one visual stimulus by increasing or decreasing at least one value for the at least one parameter for the at least one part of the at least one visual stimulus between a lower value and an upper value in a monotonous manner, or between the upper value and the lower value in a monotonous manner,
wherein the upper value is selected to elicit the at least one type of eye movements in the at least one eye of the person,
wherein the lower value is selected not to elicit the at least one type of eye movements in the at least one eye of the person, and
wherein continuously modifying the at least one part of the at least one visual stimulus is performed as a variation in which a sign of a first derivative of the variation does not change during the course of the variation.

12. A device for determining a visual performance of at least one eye of a person, the device comprising:
at least one screen, wherein the at least one screen is designated for displaying to at least one eye of a person at least one visual stimulus configured to elicit at least one type of eye movements in the at least one eye of the person;
at least one eye tracker, wherein the at least one eye tracker is designated for tracking the at least one type of eye movements in the at least one eye of the person; and
at least one processing unit, wherein the at least one processing unit is designated for determining the visual performance of the at least one eye of the person by using at least one first piece of information about the at least one visual stimulus and at least one second piece of information about an occurrence of the at least one type of eye movements in the at least one eye of the person,
wherein the at least one screen is designated for displaying at least a part of the at least one visual stimulus in a time-varying manner, whereby the at least one visual stimulus is presented in a manner that the at least one part of at the least one visual stimulus varies an appearance of the at least one visual stimulus to the at least one eye of the person over time, independent of whether the at least one type of eye movements is elicited in the at least one eye of the person or not,
wherein the at least one screen is designated for displaying the at least one part of the at least one visual stimulus by continuously modifying the at least one part of the at least one visual stimulus by increasing or decreasing the at least one value for the at least one parameter for the at least one part of the at least one visual stimulus between a lower value and an upper value in a monotonous manner, or between the upper value and the lower value in a monotonous manner,
wherein the upper value is selected to elicit the at least one type of eye movements in the at least one eye of the person,
wherein the lower value is selected not to elicit the at least one type of eye movements in the at least one eye of the person, and
wherein continuously modifying the at least one part of the at least one visual stimulus occurs from frame to frame is performed as a variation in which a sign of a first derivative of the variation does not change during the course of the variation.

13. The device according to claim 12, further comprising at least one of:
- a distance measuring unit configured to measure a distance between the screen displaying the at least one visual stimulus and the at least one eye of the person;
- a luminance sensor configured to measure a luminance level of the at least one visual stimulus, wherein the processing unit is further designated for determining the visual performance of the at least one eye of the person by using a measured value for the luminance level of the visual stimulus,
- a communication unit configured to at least one of:
  - forward data related to the tracking of the at least one type of eye movements in the at least one eye of the person to at least one external storage unit and to receive the data related to the tracking of the at least one type of eye movements from the at least one external storage unit for further processing by the processing unit; or
  - forward data related to the tracking of the at least one type of eye movements in the at least one eye of the person and further data related to the visual stimulus configured to elicit the at least one type of eye movements in the at least one eye of the person to at least one external processing unit and to receive still further data related to the visual performance of the at least one eye of the person from the at least one external processing unit.

* * * * *